(12) United States Patent
Kung

(10) Patent No.: US 7,914,436 B1
(45) Date of Patent: Mar. 29, 2011

(54) METHOD AND APPARATUS FOR PUMPING BLOOD

(75) Inventor: Robert T. V. Kung, Andover, MA (US)

(73) Assignee: Abiomed, Inc., Danvers, MA (US)

( * ) Notice: Subject to any disclaimer, the term of this patent is extended or adjusted under 35 U.S.C. 154(b) by 1176 days.

(21) Appl. No.: 11/451,221

(22) Filed: Jun. 12, 2006

(51) Int. Cl.
*A61N 1/362* (2006.01)

(52) U.S. Cl. ........................................................ 600/18

(58) Field of Classification Search ............... 417/394; 600/18, 16; 604/102.01, 264, 153, 509
See application file for complete search history.

(56) References Cited

U.S. PATENT DOCUMENTS

| | | |
|---|---|---|
| 4,014,317 A | 3/1977 | Bruno |
| 4,015,590 A | 4/1977 | Normann |
| 4,077,394 A | 3/1978 | McCurdy |
| 4,080,958 A | 3/1978 | Bregman et al. |
| 4,154,227 A | 5/1979 | Krause et al. |
| 4,407,271 A | 10/1983 | Schiff |
| 4,522,195 A | 6/1985 | Schiff |
| 4,625,712 A | 12/1986 | Wampler |
| 4,692,148 A | 9/1987 | Kantrowitz et al. |
| 4,697,574 A | 10/1987 | Karcher et al. |
| 4,741,328 A | 5/1988 | Gabbay |
| 4,785,795 A | 11/1988 | Singh |
| 4,817,586 A | 4/1989 | Wampler |
| 4,902,272 A | 2/1990 | Milder et al. |
| 4,902,273 A | 2/1990 | Choy et al. |
| 4,906,229 A | 3/1990 | Wampler |
| 4,919,647 A | 4/1990 | Nash |
| 4,943,275 A | 7/1990 | Stricker |
| 4,994,018 A | 2/1991 | Saper |
| 5,090,957 A | 2/1992 | Moutafis et al. |
| 5,116,305 A | 5/1992 | Milder et al. |
| 5,147,370 A | 9/1992 | McNamara et al. |
| 5,176,619 A | 1/1993 | Segalowitz |
| 5,308,319 A | 5/1994 | Ide et al. |
| 5,413,549 A | 5/1995 | Leschinsky |
| 5,443,451 A * | 8/1995 | Chapman et al. ............. 604/153 |
| 5,643,172 A * | 7/1997 | Kung et al. ..................... 600/16 |
| 5,820,542 A | 10/1998 | Dobak, III et al. |
| 5,827,171 A | 10/1998 | Dobak, III et al. |
| 5,891,102 A | 4/1999 | Hiejima et al. |
| 5,911,685 A | 6/1999 | Siess et al. |
| 5,911,702 A * | 6/1999 | Romley et al. ................ 604/509 |
| 5,928,132 A | 7/1999 | Leschinsky |
| 5,971,911 A | 10/1999 | Wilk |
| 6,004,258 A | 12/1999 | Watari et al. |
| 6,007,479 A | 12/1999 | Rottenberg et al. |

(Continued)

*Primary Examiner* — George Manuel
*Assistant Examiner* — Robert N Wieland
(74) *Attorney, Agent, or Firm* — Foley & Lardner LLP

(57) ABSTRACT

At least one aspect of the invention is directed to a pump system for pumping blood though a body passageway. The pump system includes a distal section having at least one inlet to receive blood, a pumping section in fluid communication with the distal section to receive blood from the distal section, and a pump constructed and arranged to be positioned within the pumping section to draw blood into the pumping section in a first phase of operation and to pump blood out of the at least one outlet valve in a second phase of operation. The pump system may be configured such that the at least one inlet is in fluid communication with the pumping section in both the first phase of operation and the second phase of operation. At least one other aspect of the invention is directed to a pump system for pumping blood from one of the right atrium and the right ventricle to the pulmonary artery.

54 Claims, 12 Drawing Sheets

U.S. PATENT DOCUMENTS

| | | |
|---|---|---|
| 6,139,487 A | 10/2000 | Siess |
| 6,176,848 B1 | 1/2001 | Rau et al. |
| 6,190,357 B1 * | 2/2001 | Ferrari et al. ............ 604/102.01 |
| 6,210,318 B1 | 4/2001 | Lederman |
| 6,231,598 B1 | 5/2001 | Berry et al. |
| 6,245,008 B1 | 6/2001 | Leschinsky et al. |
| 6,312,443 B1 | 11/2001 | Stone |
| 6,464,720 B2 | 10/2002 | Boatman et al. |
| 6,468,200 B1 | 10/2002 | Fischi |
| 6,511,412 B1 | 1/2003 | Freed et al. |
| 6,511,413 B2 | 1/2003 | Landesberg |
| 6,666,814 B2 | 12/2003 | Downey et al. |
| 6,790,171 B1 | 9/2004 | Gründeman et al. |
| 6,814,715 B2 | 11/2004 | Bonutti et al. |
| 6,858,001 B1 | 2/2005 | Aboul-Hosn |
| 7,374,531 B1 * | 5/2008 | Kantrowitz ................. 600/18 |
| 2007/0066943 A1 * | 3/2007 | Prasad et al. ................. 604/264 |
| 2007/0177997 A1 * | 8/2007 | Gharib et al. ................. 417/394 |

* cited by examiner

METHOD AND APPARATUS FOR PUMPING BLOOD

BACKGROUND OF INVENTION

1. Field of Invention

Embodiments of the invention relate generally, but are not limited to, methods and apparatus for pumping blood.

2. Discussion of Related Art

In the treatment of a number of medical conditions, it is often desirable or necessary to aid blood flow in a patient. For example, during the performance of certain surgical procedures involving the heart, external devices may be needed to aid in the circulation of blood through the body. In other situations, the body may be incapable of sufficiently providing blood flow due to a failing, traumatized or infarcted heart.

Numerous devices have been developed that may replace portions of the heart and/or provide temporary or permanent assistance to the heart and increase the flow of blood through the body. These devices include cardiac assist pumping balloons that may be inserted into any large artery, such as the femoral artery, as part of a standard catheterization procedure. Cardiac assist pumping balloons are particularly advantageous in that implementation of these devices does not typically require major thoracic or otherwise invasive surgery. Catheter based balloon pumps have been primarily used to provide minimal cardiac support by reducing afterload to the heart.

Other balloon pumps have been used to pump blood from the heart. However, typically these devices have required the use of numerous input and output valves. One example of a balloon pump using an input valve is provided in U.S. Pat. No. 5,928,132 to Leschinsky, which is incorporated by reference herein. The use of input valves in balloon pumps can increase the cost and reduce the reliability of the pumps and may provide undesirable resistance to blood flow. One drawback with typical blood pumps designed for percutaneous insertion is that size limitations dictated by the insertion method limit the flow rate of blood from these devices, and pressure drops associated with input valves can become significant in small diameter tubes used in percutaneous blood pumps.

SUMMARY OF INVENTION

At least some embodiments of the invention are directed to systems and methods for pumping blood through the body. In particular, at least one embodiment is directed to a system for pumping blood that utilizes an improved balloon pump.

A first aspect of the invention is directed to a pump system for pumping blood through a body passageway. The pump system includes a distal section having at least one inlet to receive blood, a pumping section in fluid communication with the distal section to receive blood from the distal section, the pumping section having at least one outlet valve; and a pump constructed and arranged to be positioned within the pumping section to draw blood into the pumping section in a first phase of operation and to pump blood out of the at least one outlet valve in a second phase of operation. The pump system may be configured such that the at least one inlet is in fluid communication with the pumping section in both the first phase of operation and the second phase of operation.

The pumping section and the distal section may be configured such that in the second phase of operation, a blood flow rate out of the at least one outlet valve is greater than a blood flow rate out of the at least one inlet. The pump may include a balloon that is deflating during the first phase of operation and inflating during the second phase of operation. The balloon may be coupled to a lumen to supply a medium to the balloon to inflate the balloon and to extract the medium to deflate the balloon. The pump system may be constructed and arranged to allow percutaneous insertion of at least the distal section and the pumping section into an artery of a patient. The pumping section may include an expandable cannula. The expandable cannula may include a channel that is configured to receive a filling medium to expand the expandable cannula. The pump system may include at least one anchoring device coupled to at least one of the distal section and the pumping section, wherein the anchoring device is configurable to support the pumping section in an artery of a patient. The at least one anchoring device may include a balloon that is expandable to support the pumping section in the artery. The pump system may further include an extraction device constructed and arranged to receive the expandable cannula for extraction of the expandable cannula from a patient. The extraction device may be constructed and arranged to collapse the expandable cannula as the expandable cannula is drawn into the extraction device for removal from the artery. The first phase of operation may be longer in time than the second phase of operation. The distal section may be expandable.

Another aspect of the invention is directed to a method of pumping blood in a patient. The method includes inserting a cannula into an artery of a patient, the cannula having a distal end with an opening and a pumping portion, the pumping portion being in fluid communication with the opening in the distal end and the pumping portion having at least one outlet, drawing blood through the opening and into the pumping portion in a first phase of operation, and pumping blood out of the at least one outlet and out of the opening in a second phase of operation.

In the method, pumping blood may include pumping blood out of the at least one outlet at a first flow rate and pumping blood out of the opening at a second flow rate, wherein the first flow rate is greater than the second flow rate. In the method, blood may be pumped in a cyclical manner alternating between the first phase of operation and the second phase of operation with a period of operation in the first phase being greater than a period of operation in the second phase. In the method, inserting the cannula may include positioning the distal end in the left ventricle of the patient's heart. Inserting the cannula may include inserting the cannula into the femoral artery of the patient. The pumping portion may include an expandable section, and the method may further include expanding the expandable section from an insertion state to an operational state after inserting the cannula into the femoral artery. In the method, pumping blood may include inflating a balloon located in the pumping portion, and inserting the cannula may include positioning the pumping portion in the ascending aorta of the patient. The cannula may include at least one anchoring device, and the method may further include using the at least one anchoring device to support the pumping portion in the ascending aorta. The method may further include moving the expandable section from the operational state to the insertion state by sliding the expandable section into an extraction device.

Another aspect of the invention may be directed to a pump system for pumping blood through a body passageway. The pump system includes a distal section having at least one inlet to receive blood, a pumping section in fluid communication with the distal section to receive blood from the distal section, the pumping section having at least one outlet valve, means for drawing blood into the pumping section in a first phase of operation and for pumping blood out of the at least one outlet valve in a second phase of operation, such that the at least one inlet is in fluid communication with the pumping section in both the first phase of operation and the second phase of operation.

The means for drawing blood may include means for drawing blood such that in the second phase of operation, a blood flow rate out of the at least one outlet valve is greater than a blood flow rate out of the at least one inlet. The pump system may be constructed and arranged to allow percutaneous insertion of at least the distal section and the pumping section into an artery of a patient. The pump system may further include means for expanding an expandable portion of the pumping section after insertion of the pumping section into an artery. The pump system may further include means for anchoring the pumping section in an artery of a patient. The pump system may include means for collapsing the expandable portion of the pumping section and withdrawing the pumping section from the artery. The distal section may be expandable.

Yet another aspect of the invention is directed to a pump system for pumping blood through a body passageway. The pump system includes a distal section having at least one inlet to receive blood, a pumping section in fluid communication with the distal section to receive blood from the distal section, the pumping section having at least one outlet valve, and a balloon pump positioned within the pumping section to draw blood into the pumping section in a first phase of operation and to pump blood out of the at least one outlet valve in a second phase of operation. The balloon pump may be constructed and arranged in the pumping section to block a fluid communication path between the pumping section and the distal section in the second phase of operation to prevent blood from exiting the at least one inlet in the second phase of operation.

The balloon pump may include a balloon coupled to a lumen to supply a medium to the balloon to inflate the balloon in the second phase of operation and to extract the medium from the balloon in the first phase of operation. The pump system may be constructed and arranged to allow percutaneous insertion of at least the distal section and the pumping section into an artery of a patient. The pumping section may include an expandable cannula. The expandable cannula may include a channel that is configured to receive a filling medium to expand the expandable cannula.

Another aspect of the invention is directed to a method of pumping blood in a patient. The method may include inserting a cannula into the artery of a patient, the cannula having a distal end with an opening, a pumping portion, a fluid communication path between the opening and the pumping portion, and a balloon disposed in the pumping portion, deflating the balloon to draw blood through the opening and into the pumping portion in a first phase of operation, and inflating the balloon to pump blood out of the pumping portion in a second phase of operation. In the method, inflating the balloon may include blocking the fluid communication path with a portion of the balloon.

The pumping portion may include at least one outflow valve, and inflating the balloon may include pumping blood out of the at least one outflow valve. In the method, inserting the cannula may include positioning the distal end in the left ventricle of the patient's heart. Further, inserting the cannula may include inserting the cannula into the femoral artery of the patient. The pumping portion may include an expandable section, and the method may further include expanding the expandable section from an insertion state to an operational state after inserting the cannula into the artery. In the method, inserting the cannula may include positioning the pumping portion in the ascending aorta of the patient. The cannula may include at least one anchoring device, and the method may further include using the at least one anchoring device to support the pumping portion in the ascending aorta. The method may further include moving the expandable section from the operational state to the insertion state by sliding the expandable section into an extraction device.

Another aspect of the invention is directed to a pump system for pumping blood from a patient's right atrium or right ventricle to a patient's pulmonary artery. The pump system includes a distal section having at least one outlet, a pumping section in fluid communication with the distal section to provide blood to the outlet of the distal section, the pumping section having at least one inlet valve to receive blood, and a pump constructed and arranged to be positioned within the pumping section to draw blood into the pumping section in a first phase of operation and to pump blood out of the outlet of the distal section in a second phase of operation.

The pump may include a balloon that is deflated in the first phase of operation and inflated in the second phase of operation. The balloon may be coupled to a lumen to supply a medium to the balloon to inflate the balloon. The pump system may be constructed and arranged to allow percutaneous insertion of at least the distal section and the pumping section. The pumping section may include an expandable cannula. The expandable cannula may include a channel that is configured to receive a filling medium to expand the expandable cannula. The at least one inlet valve may be a one-way valve configured to permit flow of blood into the pumping section and prevent flow of blood out of the pumping section.

Still another aspect of the invention is directed to a method of pumping blood from a patient's right atrium or right ventricle to a patient's pulmonary artery. The method includes inserting a cannula into the patient, the cannula having a distal end with at least one outlet and a pumping portion, the pumping portion being in fluid communication with the opening in the distal end and the pumping portion having at least one inlet, drawing blood from the right atrium or the right ventricle through the at least one inlet and into the pumping portion in a first phase of operation, and pumping blood out of the at least one outlet into the pulmonary artery in a second phase of operation.

In the method, inserting the cannula may include positioning the distal end in the pulmonary artery and positioning the pumping portion in the right atrium or the right ventricle. The pumping portion may include an expandable section, and the method may further include expanding the expandable section from an insertion state to an operational state after inserting the cannula into the patient. In the method, pumping blood may include inflating a balloon located in the pumping portion.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1A:
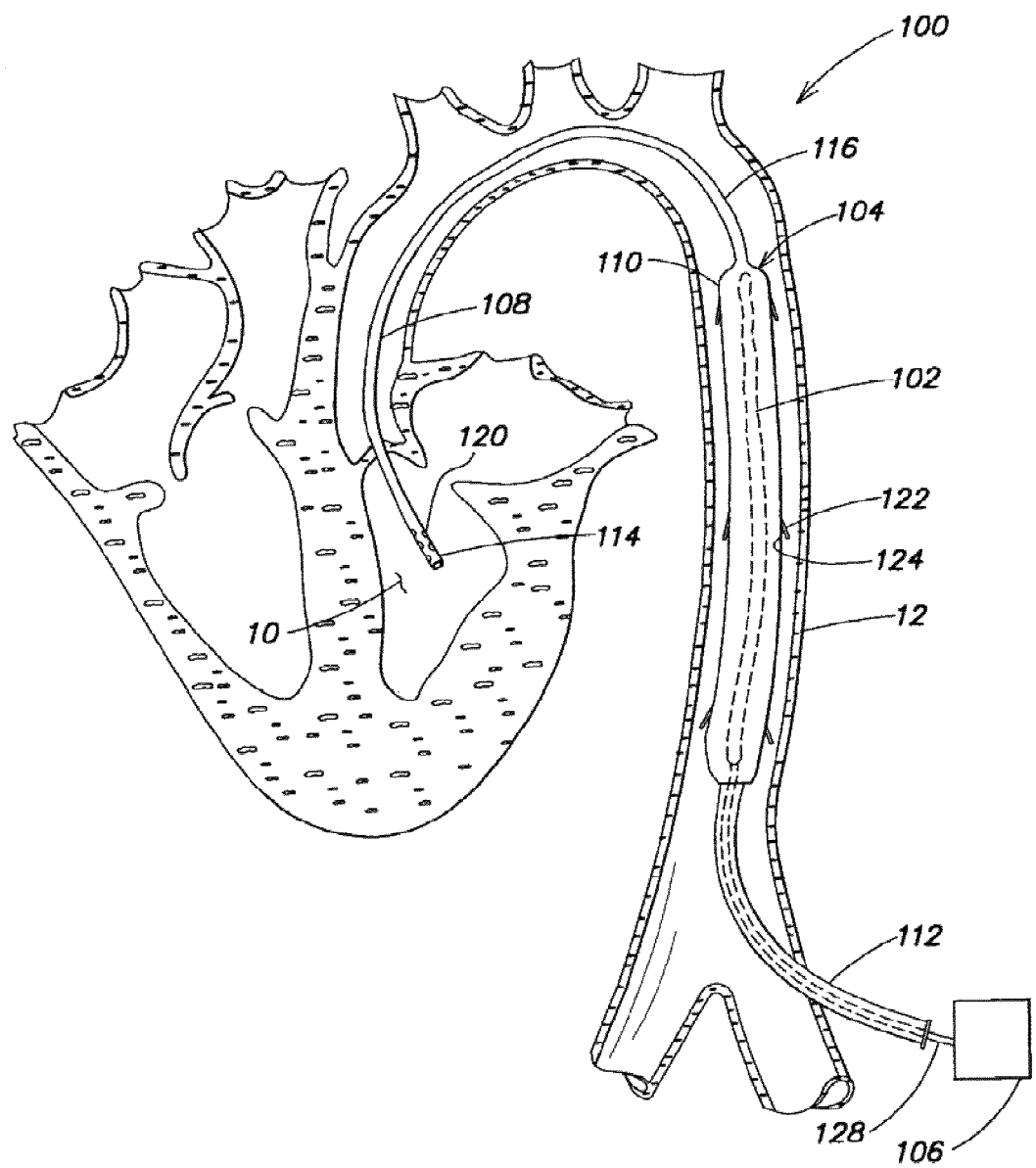
FIG. 1A shows a blood pumping system of one embodiment implanted in the left ventricle and the descending aorta of a patient.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

At least one embodiment of the invention described below provides a balloon pump disposed within an expandable cannula that may be percutaneously introduced into a major artery such as the femoral artery for use as a left ventricle assist device or as a replacement pump for a failed left ventricle. When used with the left ventricle, at least one embodiment provides a catheter based system that pumps blood from the left ventricle to the aorta. In other embodiments, balloon pumps are used to pump blood from the right atrium or ventricle to the pulmonary artery. Further, while embodiments below are described as being percutaneously introduced into the body, in other embodiments, other techniques may be used to insert devices of the present invention into the body. In embodiments described below, the terms distal and proximal are used to describe portions of devices. In general, the term distal or distal end refers to a portion of a device that is furthest from an insertion point of the device, while the term proximal or proximal end refers to a portion of a device that is closest to the insertion point.

Figure 1B:
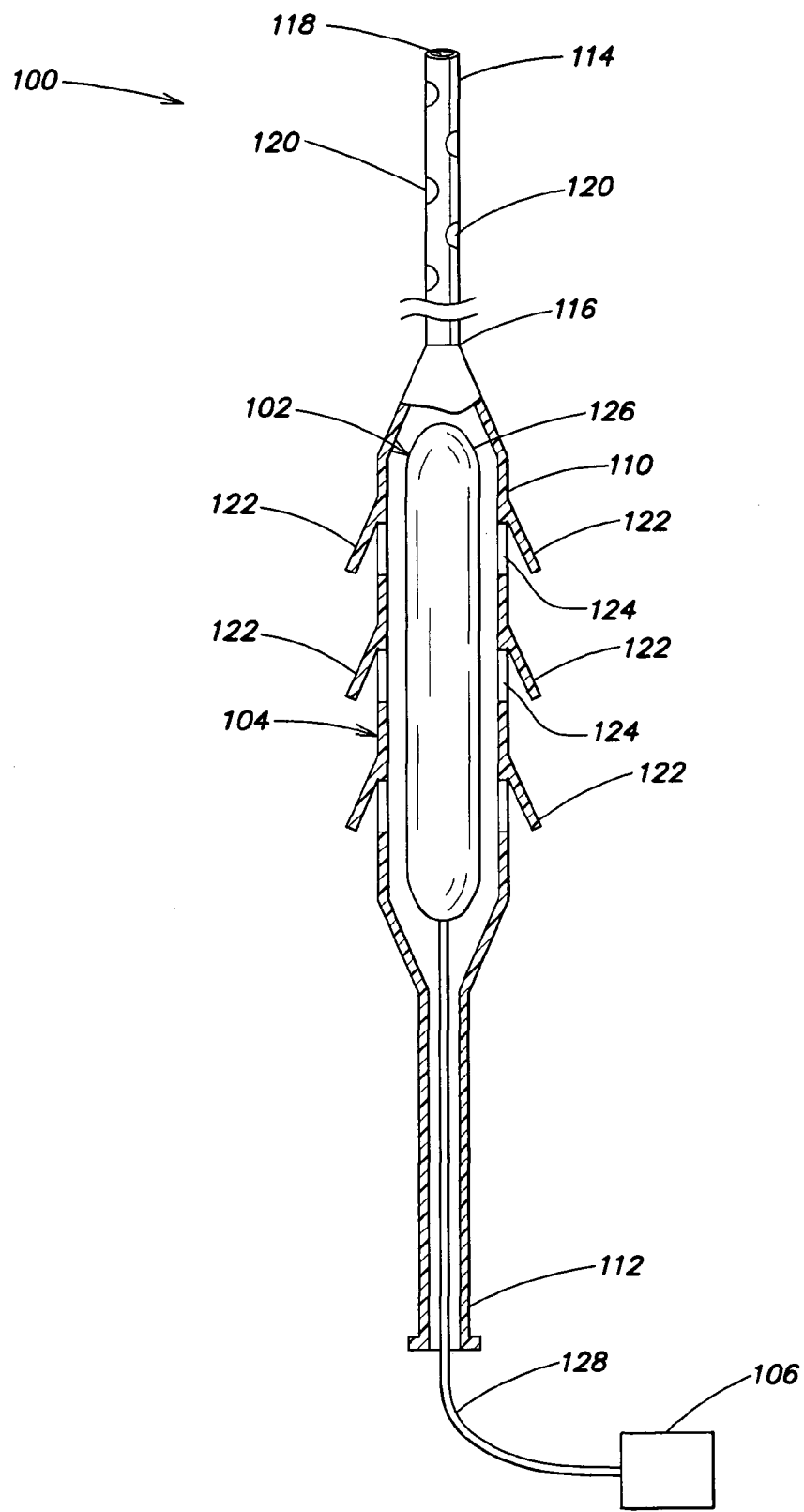
FIG. 1B shows the blood pumping system of FIG. 1 in a deployed configuration but outside of the body.

One embodiment of a blood pumping system 100 that may be percutaneously introduced into the body will now be described with reference to FIGS. 1A and 1B. FIG. 1A shows the blood pumping system 100 located in the left ventricle 10 and the descending aorta 12 of a patient, while FIG. 1B shows the system 100 in its expanded configuration, but outside of the body. The system includes a balloon pump 102 contained within a cannula 104, and a control device 106 for controlling operation of the balloon pump.

The cannula 104 includes three sections, a distal section 108, an expandable section 110 and a proximal section 112. In one embodiment, the cannula is compatible with a 15 Fr catheter insertion system and can be percutaneously inserted using known techniques. However, in other embodiments, the cannula may be larger or smaller depending on desired blood flow.

The distal section 108 of the cannula is implemented in one embodiment using a flexible small diameter tube having a distal end 114 and a proximal end 116. The distal end 114 has an end inlet 118 and side inlets 120. In one embodiment, the distal section has a diameter of 5 mm with a wall thickness of 0.1 mm and three to four side inlets are included with each of the side inlets and the end inlet having a circular opening 4.8 mm in diameter. In other embodiments, other sizes may be used. The use of a small diameter flexible tube for the distal portion of the cannulla allows the distal end to easily bend around the aortic arch and be inserted through the aortic valve and into the left ventricle. A standard pigtail configuration may be incorporated at the distal end to facilitate the crossing of the aortic valve. To limit the pressure drop in the small diameter tube, in one embodiment, the length is kept to a minimum, and in other embodiments, the inner diameter of the distal section may be tapered to provide a larger inner diameter at the portion of the distal section that connects to the expandable section 110. In this embodiment, the taper allows the portion of the distal section that is flexed through the aortic arch to be sufficiently flexible without unnecessarily limiting the inner diameter of the portion of the distal section that is closest to the expandable section. In another embodiment, the distal section may be expandable to increase its diameter to allow higher flow rates. The distal section may be expanded using mechanisms similar to those described below for the expandable section.

The expandable section 110 is coupled between the distal section 108 and the proximal section 112. The expandable section has a distal end that couples to the distal section 108 and a proximal end that couples to the proximal section 112. In the embodiment shown in FIGS. 1A and 1B, the expandable section includes six one-way valves 122 that cover openings 124. The one-way valves are configured to open and close based on the pressure differential between the interior of the expandable section and the interior of the aorta. During operation of the blood pump, when the pump deflates (as described below), the valves move to a closed position covering the openings, and when the pump expands, the valves move to an open position exposing the openings. In one embodiment, the valves are implemented using flapper valves covering openings and the area of the openings under the valves is much greater than the area of openings of the side inlets and the end inlet of the distal section. In other embodiments, other types of valves may be used, and the number of valves and openings in the expandable cannula may be more or less than six.

The expandable portion in at least one embodiment is implemented using a thin walled expandable cannula having an outer wall with an expanded outer diameter that is comparable in size to, but smaller than, the inner lumen of the descending aorta. The expanded section is designed to withstand vacuum of at least −100 mmHg created during operation of the pump without any collapse of the outer wall. In one embodiment, the expanded section is 10 to 15 cm long, 1.5 to 2 cm in diameter (when expanded), has a wall thickness of 0.1 mm and is made from polyethylene, polyurethane or polyvinyl chloride (PVC). However, in other embodiments, other sizes may be used, and the expanded section may be made from other materials.

In the embodiment shown in FIGS. 1A and 1B, the proximal end of the expandable section of the cannula tapers down to a size that is compatible with percutaneous introduction. In one embodiment for use with a 15 Fr catheter system the outer diameter at the proximal end is 5 mm with a wall thickness of 0.1 mm. However, the proximal end may be sized differently for use with other catheter systems. As described further below, the expandable portion of the cannula may include a deployable metal mesh, a coiled spring or fluid fillable channels to provide for expansion and retraction of the expandable portion. As described below, in at least one embodiment, the expandable section may be wrapped for implantation and extraction with a resulting outer diameter in the wrapped state that is comparable to the outer diameter of the proximal section.

The proximal section 112 of the cannula mates with the proximal end of the expandable section. In one embodiment, the proximal section has an outer diameter of 5 mm and a wall thickness of 0.1 mm and is compatible with a 15 Fr catheter system. Further, in at least one embodiment, the proximal section 112 is constructed from polyethylene, polyurethane or PVC.

The balloon pump 102 includes a balloon 126, a tube 128 and the control device 106. The tube 128 is coupled to the balloon and includes a balloon port for coupling to the control device. In at least one embodiment, the balloon is made from polyethylene, polyurethane or PVC and is elongated to fit within the expandable section 110 when the balloon is expanded.

In one embodiment, the balloon has a volume of approximately 40 to 50 cc when filled, however, in other embodiments, the particular shape and size of the balloon may be different. The tube 128 is used to fill the balloon from gas supplied by the control device 106. In at least one embodiment, the tube is a 7 Fr lumen, however, depending on the desired pumping rate of the balloon, other sizes may be used. In one embodiment, a seal is provided between the proximal section of the cannula and the tube 128 to prevent any blood from leaking out of the proximal portion, however, the seal may be located in other positions as well. In other embodiments, the tube 128 may be integral with the proximal section with an inner portion of the proximal section coupled directly to the balloon.

The control device 106 may include an air pump, one or more inputs to receive data related to the patient, such as heartbeat rate, and the timing of the systolic and diastolic periods of the patient's heart, and the control device may include control electronics to control the filling of the balloon by the air pump. In other embodiments, pumps using helium other gases, or liquids may be used.

Operation of the blood pump system 100 will now be described. Initially, the blood pump is introduced into the aorta and is positioned as shown in FIG. 1A. Particular methods for introducing the blood pump into the aorta and placing it in the expanded state are described below. The distal section of the cannula extends into the ventricle. The expandable section is located in the descending aorta, and the proximal section extends through an incision in the femoral artery. Expansion of the expandable section sets up a chamber in which the balloon can expand and contract. At this point, the blood pump can begin operating to pump blood from the chamber of the expandable section. Once blood is drawn into the chamber of the expandable section, the control device begins to cyclically inflate and deflate the balloon to cause pressurized blood to flow through the valves when the balloon is inflated and to cause blood to flow into the chamber of the expandable section from the left ventricle when the balloon is deflated.

In the embodiment shown in FIGS. 1A and 1B, there is no valve included between the end inlet 118 and the expandable section of the cannula. While a one-way valve may be included in the distal section or the expandable section in some embodiments to prevent blood flow back through the distal section during expansions of the balloon, in at least some embodiments, the pump system 100 is designed and controlled, such that a valve in this position is not necessary.

In many prior art balloon pumps, it is necessary and/or desirable to synchronize the operation of the pump with the natural beating of the heart, such that the balloon pump pumps at the same time as the heart (synchronous operation) or pumps when the heart is not pumping (asynchronous operation, also known as counterpulsation). In embodiments of the present invention, it is not necessary to provide such synchronization, and as will become apparent from the following description, there are advantages to both synchronous operation and asynchronous operation.

Figure 2A:
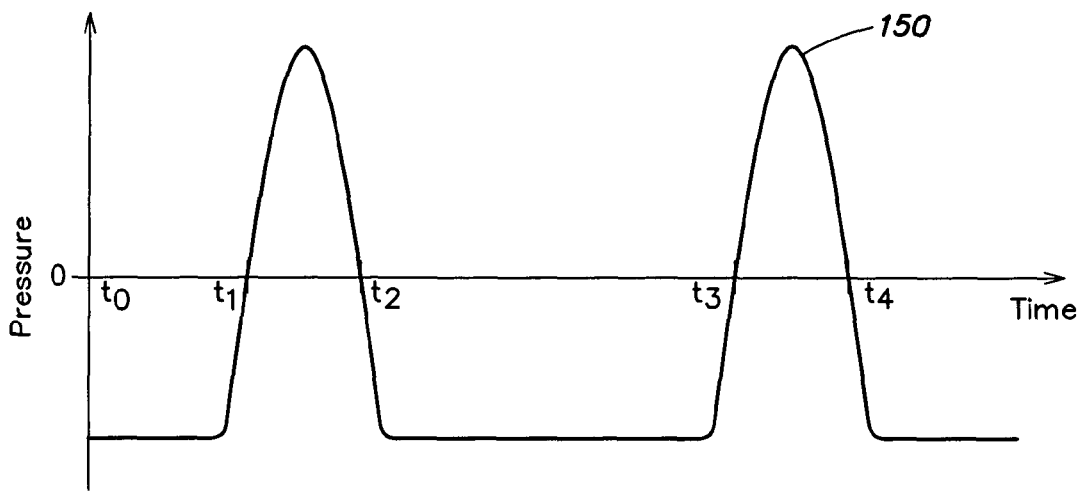
FIGS. 2A, 2B, 2C, 2D, 2E, 2F and 2G show curves of pressure and blood flow for different operating conditions of at least one embodiment.
Figure 2B:
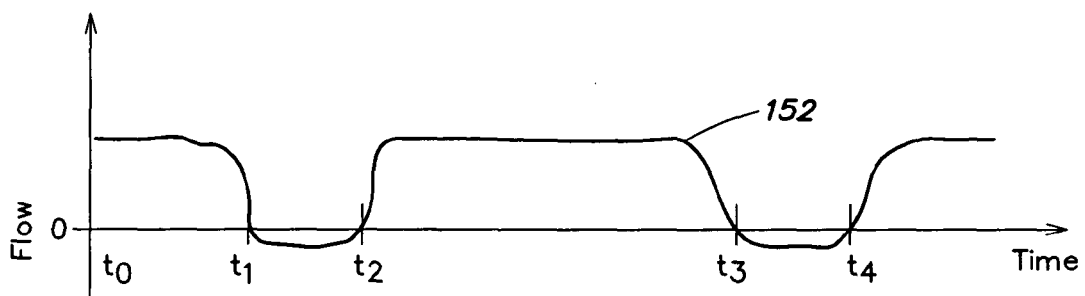
Figure 2C:
Figure 2D:
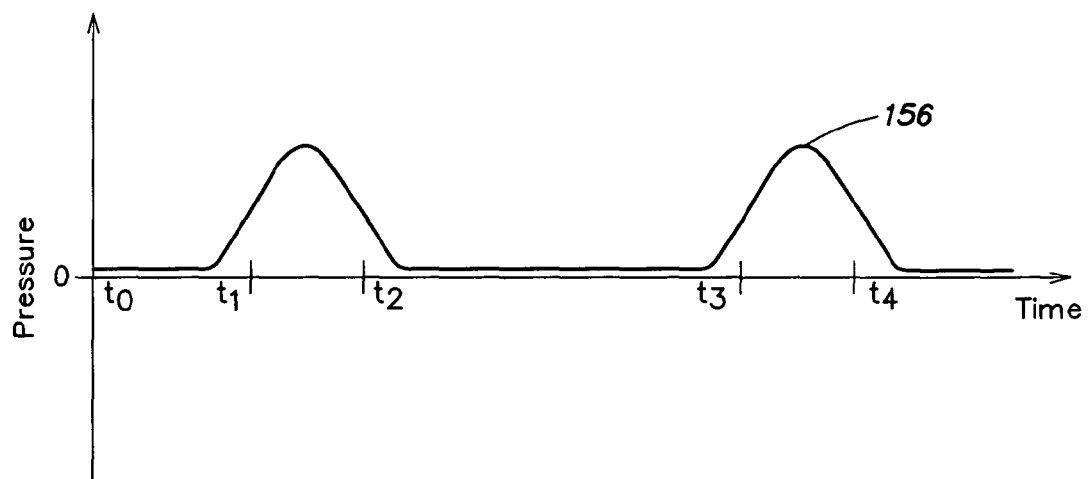
Figure 2E:
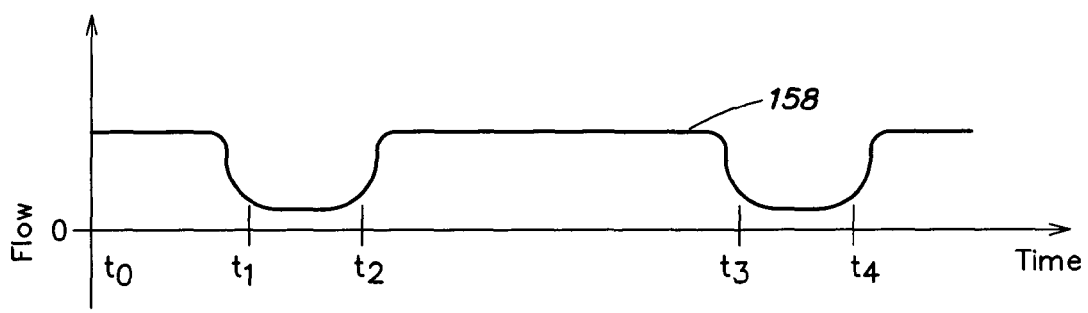

The pressure in the expandable section and the flow of blood in and out of the expandable section during operation of one embodiment will now be described with reference to FIGS. 2A-2G, which provides representative flow and pressure curves verses time. FIGS. 2A-2C will be used to describe operation of the pump system 100 with the natural heart not beating. FIGS. 2D and 2E will be used to describe operation with the pump system 100 operating synchronously with the natural heart, and FIGS. 2F and 2G will be used to describe operation when the pump system is operating asynchronously with the natural heart. As described further below, the pump system 100 may be operated at beat frequencies greater than the natural beat frequency of the heart, and the filling time of the expandable section may be considerably longer than the pumping time of the pump system.

FIG. 2A shows a plot 150 of pressure in the expandable section versus time. In FIGS. 2A-2G, the pump system 100 is pumping blood (systole) between time t1 and t2 and between time t3 and t4 and is filling (diastole) with blood from the ventricle during the remaining time between t2 and t3. During systole, the balloon expands and the pressure in the expandable section increases, and during diastole the balloon is deflated and the pressure decreases below zero. FIG. 2B shows a plot 152 of blood flow between the ventricle and the expandable section, and as shown in FIG. 2B, the flow of blood from the ventricle into the expandable section is positive during diastole, and is negative during systole as some blood flows back into the distal section and into the ventricle during pump systole. FIG. 2C shows a plot 154 of blood flow from the expandable section into the aorta. As shown in FIG. 2C, during systole, blood flows from the expandable section, and during diastole, when the output valves are closed, there is no blood flow into the aorta.

FIG. 2D shows a plot 156 of ventricular pressure verses time for a patient having an operational natural heart. As shown in FIG. 2D the increases in ventricular pressure (and the beating of the heart) are synchronous with the filling of the balloon of the pump system. During such synchronous operation, the increase in ventricular pressure (caused by the natural beating of the heart) during systole of the balloon pump reduces (and may eliminate) the regurgitation of blood out of the inlet of the pump system 100. FIG. 2E shows a plot 158 of the blood flow into the expandable section for synchronous operation. As readily apparent by comparing FIG. 2E with FIG. 2C (blood flow with no natural heart beat), the increase in ventricular pressure has eliminated the flow of blood out of the distal section and into the ventricle during systole. Actual changes in flow due to synchronous operation will depend on the strength of the natural heart as well as the pressure created in the expandable section by the filling of the balloon.

Figure 2F:
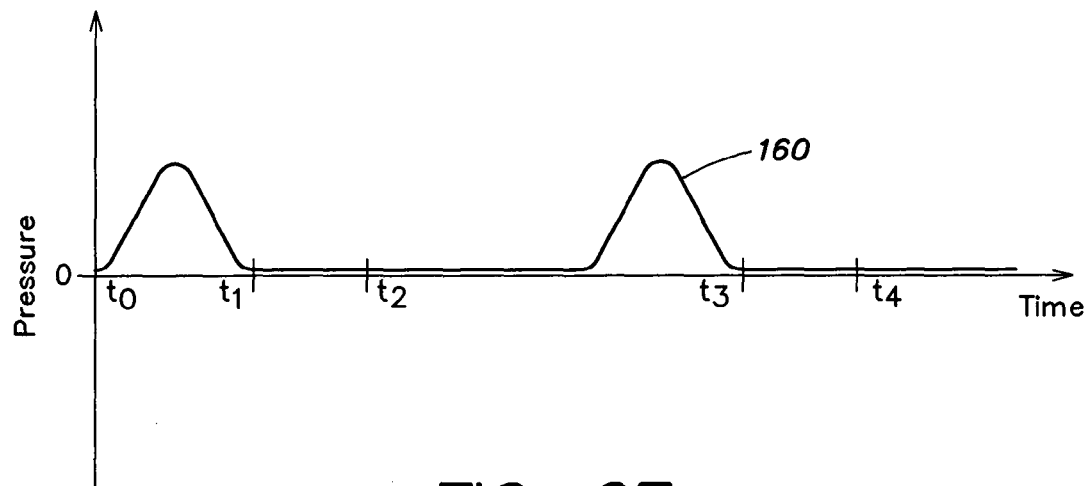
Figure 2G:
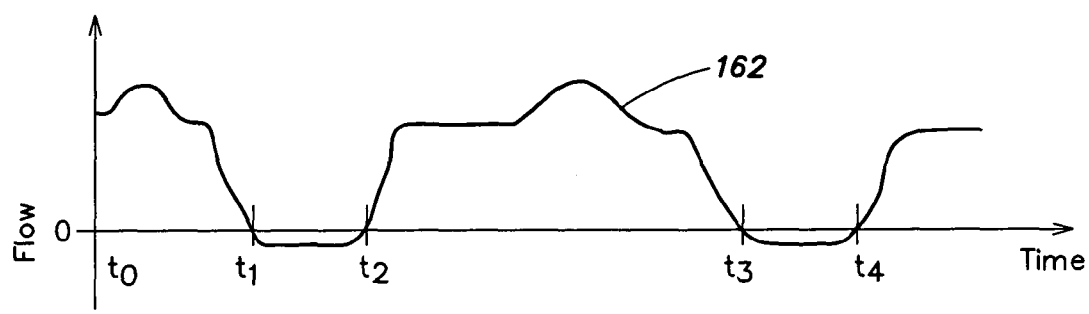

FIG. 2F shows a plot 160 of ventricular pressure for a natural heart beating asynchronously with the filling of the balloon of the balloon pump system, and FIG. 2G shows a plot 162 of blood flow into the expandable section. As indicated in FIG. 2G, the flow of blood into the expandable section will increase when the natural heart beats. This will result in an increase in the total blood that flows into the expandable section during diastole of the blood pump and an increase in blood flow from the expandable section during systole of the blood pump both into the aorta and regurgitated back into the ventricle. Based on the previous description, there are advantages for blood pump systems of the present invention for asynchronous operation and synchronous operation, and for at least some embodiments, the operation of the blood pump is not controlled based on the beating of the natural heart.

Embodiments of the present invention may be operated at different beat rates depending on the desired volume of blood to be pumped, the size of the balloon, and the size of the inner diameters of the distal portion of the catheter and the proximal portion of the catheter. The typical physiological blood flow rate for an adult is approximately 5 liters per minute (L/min), and as described below, embodiments of the invention may be sized and controlled to meet this blood flow rate. In other embodiments, the blood flow rate may be less than 5 liters per minute when a pump is used in conjunction with a heart that is partially operational.

In one embodiment, the use of an extended diastolic time, compared with the systolic time, enables longer, thinner cannula sections to be used for the inlet cannula, making it easier to install the inlet cannula into the ventricle. The systolic time is able to be relatively short (in comparison with the diastolic time) through the use of multiple one-way outflow valves in the expanded portion of the cannula. Further, in at least one embodiment, the use of a longer diastolic time allows the balloon pump system 100 to be implemented without using a one-way valve on the inlet. In one such embodiment, a 40 cc blood pump has a 5 mm cannula having a length of 10 to 15 cm for the distal section and a 1.5 to 2 cm cannula having a length of 10-15 cm for the expandable section. The pump has six to 10 outlet valves each covering a circular opening of 5 mm in diameter, and is driven by a vacuum assist of approximately −100 mmHg during diastole and approximately 100 mmHg during systole. The configuration allows a one to ten ratio to be achieved between the diastole time and the systole time. With this ratio, only approximately 10% of the blood is regurgitated through the inlet, and sufficient pumping of blood can be achieved without the use of an inflow valve. Using this ratio, to achieve a 4.0 L/min flow rate, the balloon is sized and operated at a beat rate to achieve approximately 4.4 L/min to account for the regurgitation. In one embodiment a beat rate of 120 is used. In some embodiments, to achieve higher beat rates it may be desirable to use helium as the medium for filling the balloon. As readily understood by those of skill in the art, the time required to fill the expandable chamber is dependent on the diameter and length of the inlet cannula and the pressure differential between the ventricle and the expandable section.

Figure 3A:
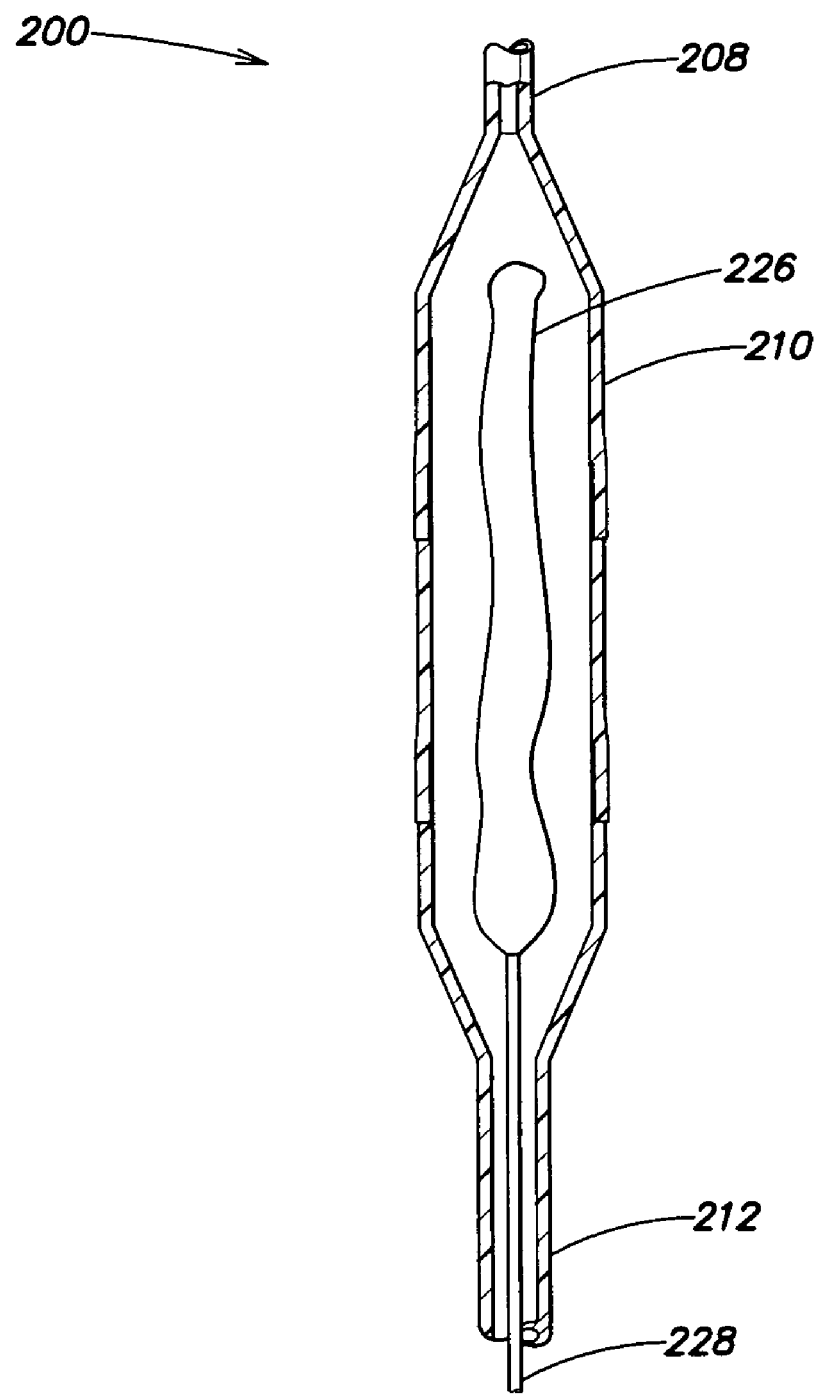
FIG. 3A shows a portion of a balloon pump in accordance with one embodiment in a deflated state.
Figure 3B:
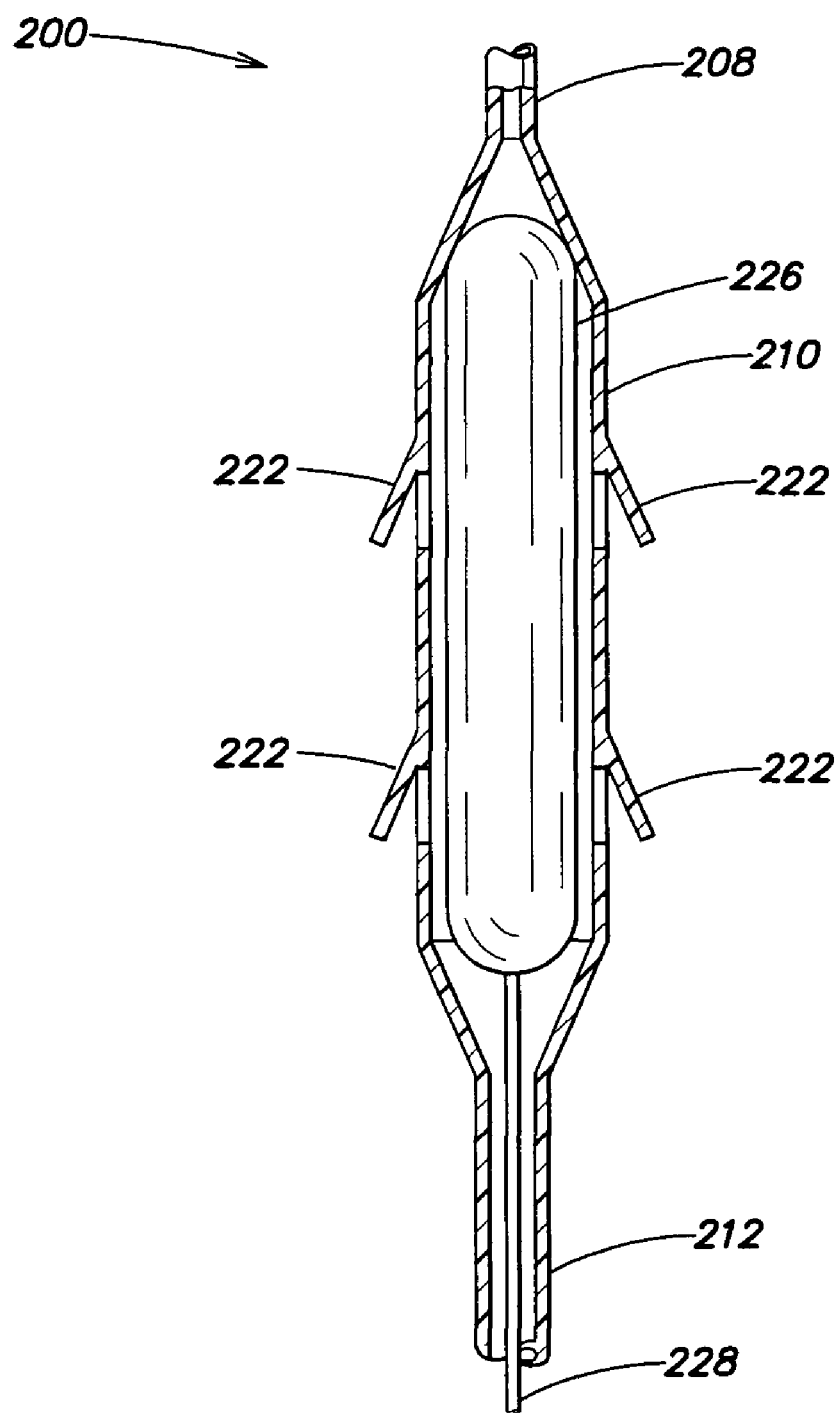
FIG. 3B shows the balloon pump of FIG. 3A in an inflated state.

In at least one embodiment described above, a balloon pump achieves physiologic flow rates without the use of a traditional inflow valve. In another embodiment, a balloon pump system 200 is provided in which the balloon 226 is used as part of a valve to prevent regurgitation and provide higher flow rates. FIGS. 3A and 3B show a section of the balloon pump system 200 including the balloon 226, an expandable section 210, a portion of a distal section 208, and a portion of a proximal section 212. The expandable section includes outflow valves 222 that are similar to the outflow valves discussed above and the balloon is coupled to a fill tube 228 in a manner similar to embodiments discussed above. The remaining parts of the balloon pump system 200 may be similar to balloon pump system 100 discussed above. FIG. 3A shows the balloon 226 in a deflated mode and FIG. 3B shows the balloon in an inflated mode.

The balloon pump system 200 operates in a manner similar to the balloon pump system 100 described above with one significant difference. In the balloon pump system 200, the balloon is positioned in the expandable section and shaped such that inflation of the balloon causes blockage of the fluid channel between the distal section and the expandable section, and in this manner, the balloon itself acts as a one-way valve to prevent regurgitation of blood out of the inlet during systole. The balloon 200 may include an inflatable tip that extends at least partially into the distal section to block the opening to the distal section upon inflation. The use of the balloon as part of a valve allows the system 200 to operate more efficiently and for a given beat rate can allow a smaller diameter distal section to be used.

Figure 4:
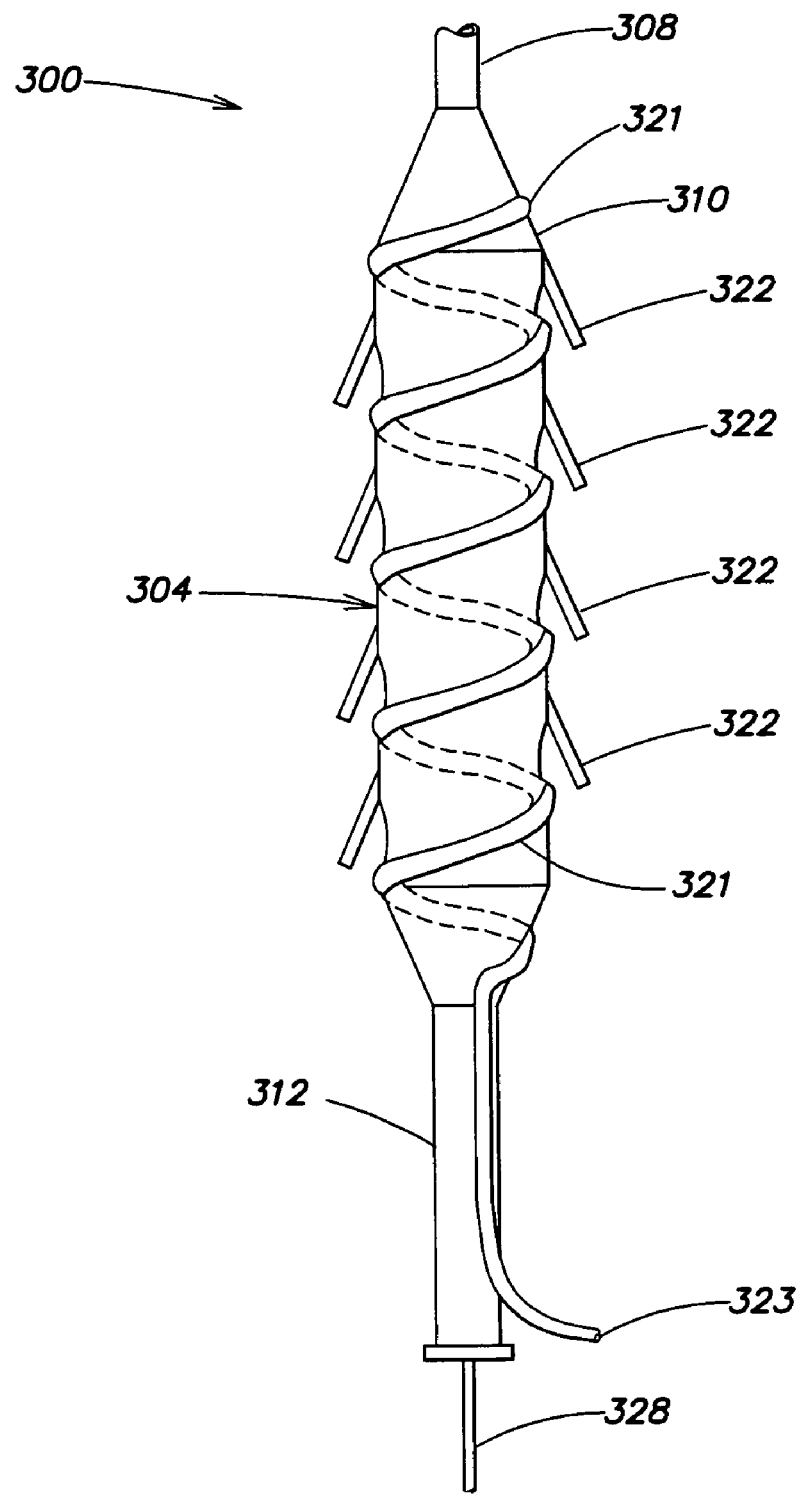
FIG. 4 shows an embodiment of a blood pumping system having an expandable pumping section.

As will now be described, at least some embodiments of balloon pumps described herein are collapsible to facilitate percutaneous implantation using for example, the standard Seldinger technique. Further, upon expansion, in at least some embodiments, reinforcement is provided to walls of the expansion section of the cannula to prevent collapse of the expansion section when the balloon deflates. FIG. 4 shows a partial perspective view of a balloon pump system 300 that is similar to embodiments of balloon pumps described above and operates in a similar manner. The balloon pump system 300 includes a distal section 308, a proximal section 312 and an expandable section 310 having valves 322. The expandable section includes a balloon which is not visible in FIG. 4. A fill tube 328 for the balloon extends into the expandable section and couples to the balloon. A helical fluid channel 321 is integrally formed or firmly attached around the exterior of the expandable section of the cannula. The fluid channel 321 is coupled to an injection port 323 that runs along the length of the proximal section and is positioned outside of the puncture site when in use. In one embodiment, the expandable section as well as the fluid channel may be made from the same material as the balloon, such as polyethylene, polyurethane or PVC.

After implantation of the cannula 304, pressurized gas or fluid is introduced into the fluid channel 321, which causes the expandable portion of the cannula to expand. During operation of the balloon pump, the fluid channel remains filled to prevent collapse of the expandable section during deflation of the balloon. In at least one embodiment, a stiffening wire may be threaded through the fluid channel to provide further support. When the cannula is to be extracted, the pressurized fluid or gas is withdrawn from the fluid channel 321 allowing the expandable section to collapse for extraction.

As discussed above, the standard Seldinger technique may be used for implantation of balloon pumps of at least some embodiments of the present invention. In one embodiment, after puncture of the femoral artery, a guide wire is inserted into the artery and moved through the artery and into the left ventricle using known techniques. The cannula 104 may then be slid over the wire until the distal section of the cannula is in place in the left ventricle.

During insertion of the cannula, in at least one embodiment, the expandable section is tightly wrapped as described below. After insertion, the wire may be withdrawn and the expandable section of the cannula may be expanded to its operating position. In one embodiment, the balloon 126 and the tube 128 are inserted into the cannula 104 after the cannula has been inserted into the body and moved to its expanded configuration. The insertion of the balloon after expansion of the cannula allows the expandable section of the cannula to be more tightly wrapped for insertion. In other embodiments, the balloon may be wrapped within the expandable section during implantation.

Figure 5:
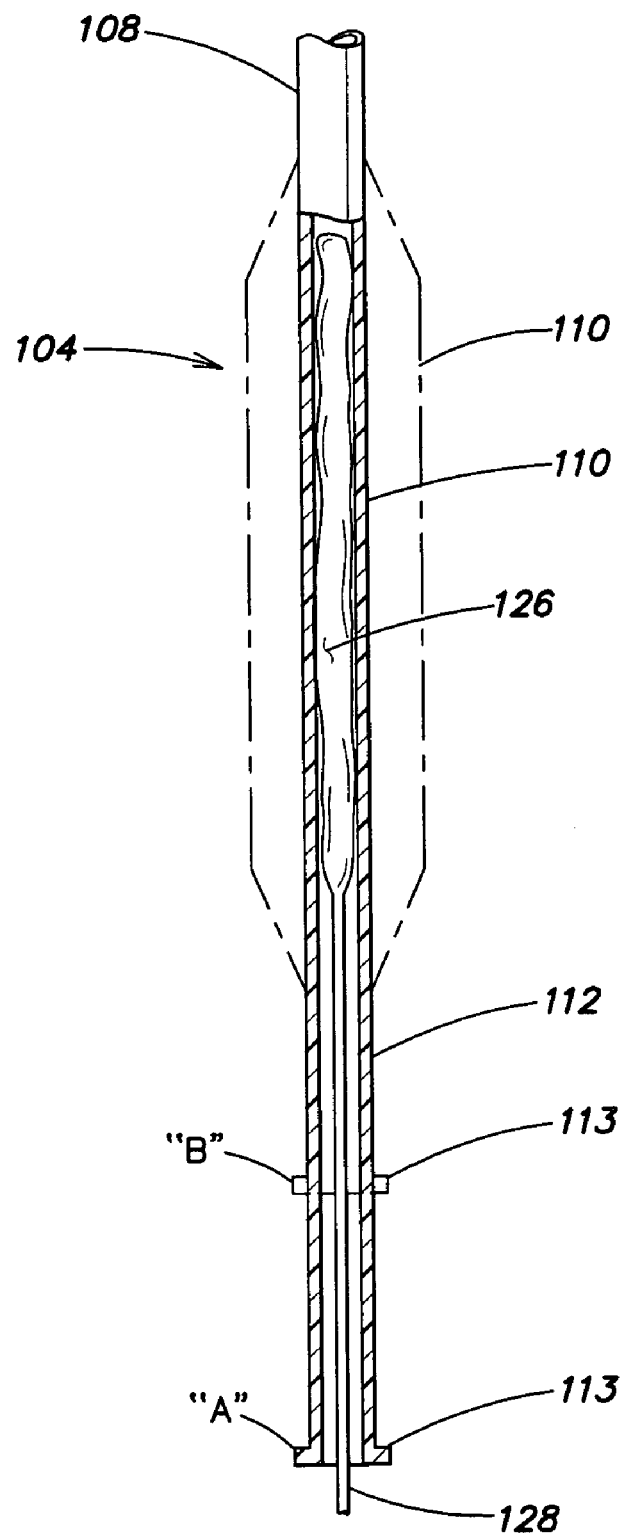
FIG. 5 shows an expandable cannula section useable in at least one embodiment.

Expansion of a cannula in accordance with at least one embodiment will now be described with reference to FIG. 5, which shows a portion of the cannula 104 discussed above. The portion shown in FIG. 5 includes the expandable section 110, a portion of the distal section 108, and the proximal section 112. The proximal section includes a cannula port 113 which is located outside of the insertion point. In FIG. 5, the expandable section 110 of the cannula 104 is shown in a wrapped or collapsed configuration for insertion into an artery in solid lines and in an expanded configuration for use in dashed lines. In the embodiment shown in FIG. 5, the balloon 126 is within the collapsed section during insertion of the cannula. As indicated in FIG. 5, upon expansion of the cannula, the cannula port 113 moves from position "A" to position "B." In moving from position "A" to position "B" the cannula port slides along the fill tube 128.

Expansion of the cannula 104 may be accomplished as described above using fluid channels 321 or in other embodiments may be accomplished using, for example, a preformed cylindrical mesh, which when stretched (for insertion) has a small diameter, but increases in diameter when allowed to resume to its natural state (during expansion). Still in other embodiments, a precoiled spring coupled to a rotating deployment mechanism outside of the insertion point may be used to expand the cannula and provide structural support for the expansion section.

Figure 6A:
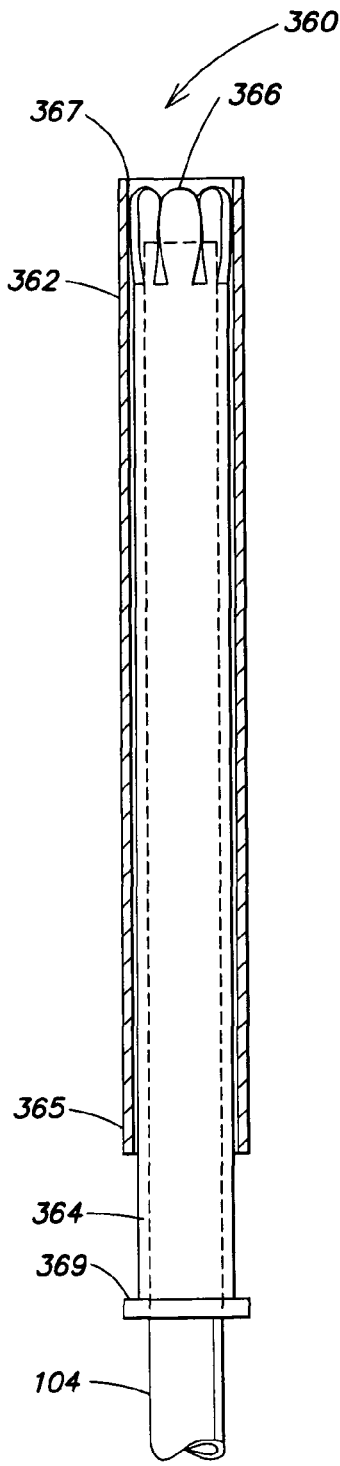
FIG. 6A shows a side view of an expandable cannula and an extraction device in accordance with at least one embodiment with the expandable cannula in a pre-wrapped configuration.
Figure 6B:
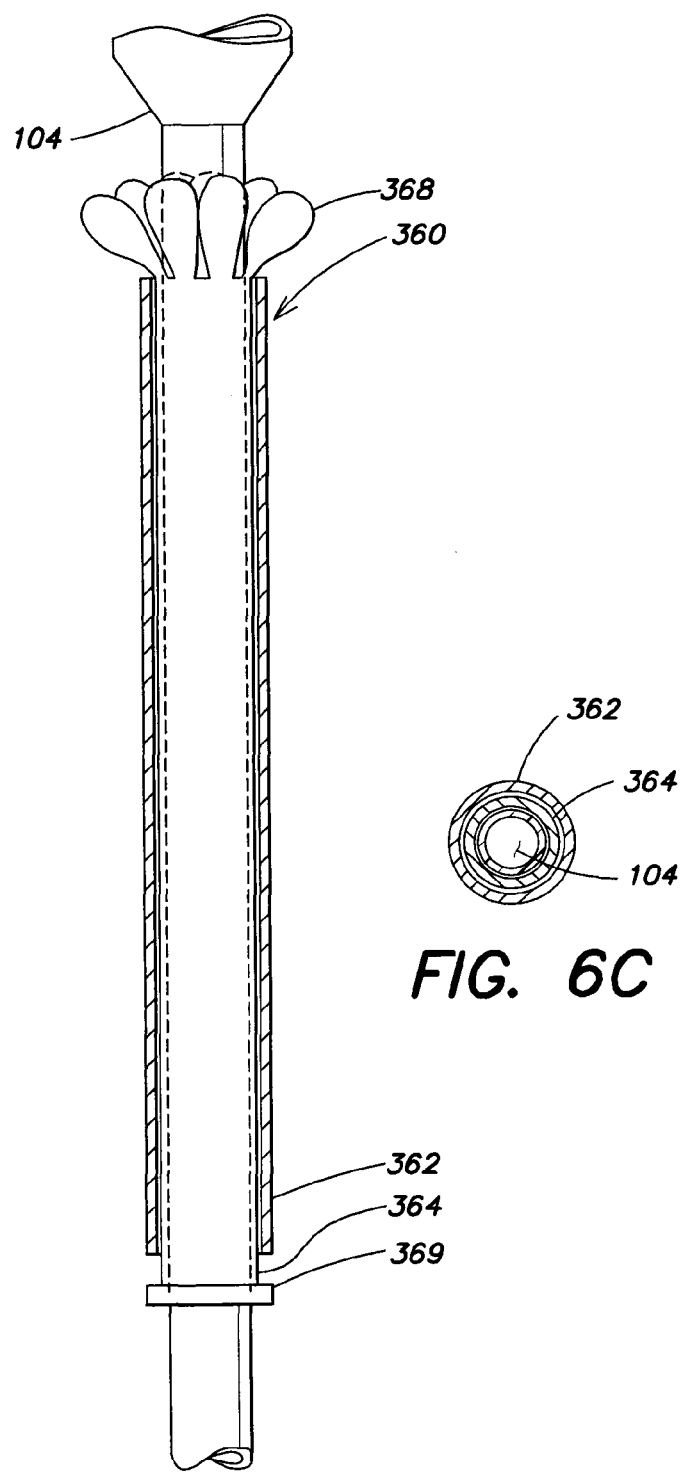
FIG. 6B shows a side view of the expandable cannula and the extraction device of FIG. 6A in a deployed state.
Figure 6C:
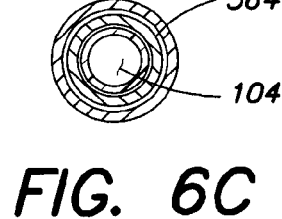
FIG. 6C shows a cross-sectional end view of the expandable cannula and extraction device of FIG. 6A.

As will now be discussed with reference to FIGS. 6A, 6B and 6C, in at least some embodiments, an extraction tube 360 is used to assist in implanting and extracting a cannula, such as cannula 104. FIG. 6A shows a cross-sectional side view of the extraction tube 360 containing the cannula 104 in a pre-deployment state with the cannula fully contained in the extraction tube, and FIG. 6B shows a cross-sectional side view of the extraction tube with the cannula 104 in a deployed expanded state. The balloon 124 may be contained in the cannula 104 in the pre-deployment state or may be inserted into the cannula after deployment of the cannula. FIG. 6C shows a cross-sectional end view of the extraction tube 360. The extraction tube 360 includes an outer tube 362 and an inner tube 364. The extraction tube includes a proximal end 365 and a distal end 367. The inner tube is positioned concentrically within the outer tube and the inner tube has a flared end 366 at the distal end having flared segments 368. The inner tube is slideable within the outer tube for deployment and retraction of the cannula 104 as described below. In at least one embodiment, the inner tube extends out of the outer tube at the proximal end, and the inner tube may include an annular ring 369 that functions as a stop mechanism to limit the distance that the inner tube may slide within the outer tube.

Prior to deployment, the cannula is contained within the extraction tube in a pre-wrapped configuration as shown in FIG. 6A. During implantation of the cannula 104, the extraction tube may be inserted through the incision with the cannula 104 in the wrapped state. In at least one embodiment, the length of the extraction tube may be substantially less than the length of the cannula 104, such that during implantation, the proximal end of the cannula extends out of the proximal end of the extraction tube, with the distal end of the cannula contained within the extraction tube and positioned near the distal end of the extraction tube. After inserting the extraction tube through the incision, the extraction tube may be slid through an artery until its distal end is positioned at approximately the deployment site for the expansion section of the cannula 104. The cannula 104 is slid from within the extraction tube until the expansion section is in place in the artery, where it can be expanded for use. In embodiments that use a cylindrical mesh as the expansion mechanism for the expansion section of the cannula, the cylindrical mesh may be configured to expand as the cannula 104 is removed from the extraction tube.

In embodiments of the invention, the use of the extraction tube eases the process of withdrawing the cannula from the artery after use. In preparation for cannula withdrawal, the inner tube may be slid within the outer tube until the annular ring 369 contacts the outer tube to push the flared segments 368 out of the distal end of the outer tube. In one embodiment, the inner tube is slid approximately 1 cm to expose the flared segments. Extraction of the cannula 104 begins with the deflation of the balloon 126. In one embodiment, after deflation of the balloon, the balloon is removed from the cannula 104, however, in other embodiments, the balloon may remain in the cannula 104 during the extraction process. The cannula 104 is then slid within the extraction tube such that the expandable section is pulled through the flared end of the inner tube. The inner tube functions as a funnel causing the expandable section to collapse as it is drawn into the inner tube. The cannula 104 may be completely drawn into the extraction tube at which point the extraction tube itself is withdrawn. In another embodiment, only the expanded section of the cannula 104 is withdrawn into the extraction tube prior to withdrawing the extraction tube and the remainder of the cannula 104.

Figure 7:
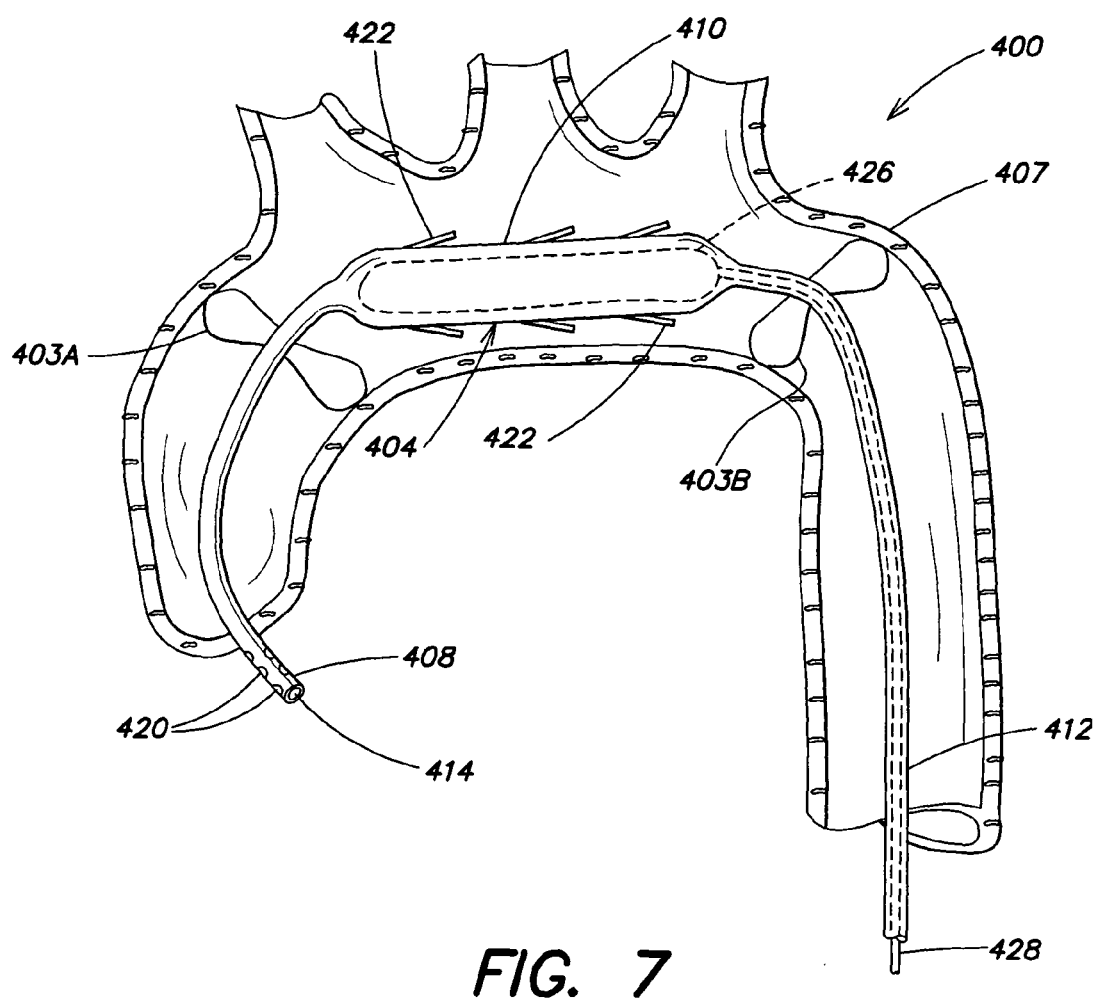
FIG. 7 is a side view of a blood pumping system in accordance with another embodiment implanted in the ascending aorta of a patient.
Figure 8:
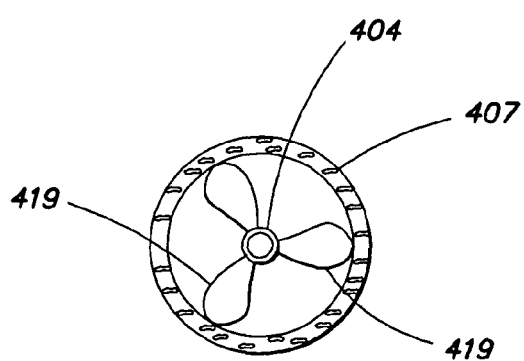
FIG. 8 is a cross-section view of an anchoring leg of the blood pumping system of FIG. 7.

Another embodiment of a balloon pump system 400 will now be described with reference to FIGS. 7 and 8. FIG. 7 shows the balloon pump system 400 implanted in a patient, while FIG. 8 shows a side view of an anchoring leg of the balloon pump system. The balloon pump system 400 includes a cannula 404 having a distal section 408, an expandable section 410 and a proximal section 412. Cannula 404 is similar to cannula 104 discussed above except that the distal section is much shorter in length. In one embodiment of the balloon pump system 400, the length of the distal section is approximately six to eight cm long. The distal section includes an end inlet 414 and side inlets 420. The expandable section includes valves 422 that cover openings 424 in a manner similar to valves 122 discussed above. The expandable section 410 includes a balloon 426 coupled to a fill tube 428. The fill tube may be coupled to a control module, such as control module 106 discussed above.

The balloon pump system 400 also includes two anchoring legs, including a distal anchoring leg 403A and a proximal anchoring leg 403B. The distal anchoring leg 403A is coupled to the cannula 404 near the junction of the distal section of the cannula and the expandable section of the cannula, and the proximal anchoring leg 403B is coupled to the cannula 404 near the junction of the expandable section of the cannula and the proximal section of the cannula. The anchoring legs are used to maintain the position of the expandable section of the cannula in approximately the center of the ascending aorta region to prevent blockage of any of the arteries exiting from this region. In one embodiment, the anchoring legs are fixed to the cannula using, for example, an adhesive, however, in other embodiments, other techniques may be used. Further, in other embodiments, the anchoring legs may be located in other locations on the cannula 404 and more or fewer anchoring legs may be used.

With reference to FIG. 8, each of the anchoring legs includes three balloons 419 that are configured to extend from the cannula to the inside of the walls of the ascending aorta 407. In one embodiment, each of the balloons 419 is coupled to a fill tube (not shown) which extends along the cannula and outside of the puncture site. After implantation of the balloon pump 400, pressurized gas or fluid may be applied to the fill tube to inflate each of the balloons. In one embodiment, in which the balloon pump includes an expansion channel, like channel 321 of balloon pump 300, the balloons are coupled to the channel 321 and are inflated and deflated with the channel 321. The balloons 419 are configured such that there is space between each of the balloons to provide blood flow through each of the anchoring legs.

Once anchored in place, balloon pump system 400 operates in a manner similar to balloon pump system 100 described above. The placement of balloon pump system 400 allows for a shorter length of the distal section which allows the balloon pump 400 to be used for higher blood flow rates. Balloon pump system 400 may be implanted and extracted using methods described above including those that use extraction tubes to facilitate the withdrawal of the cannula.

Figure 9:
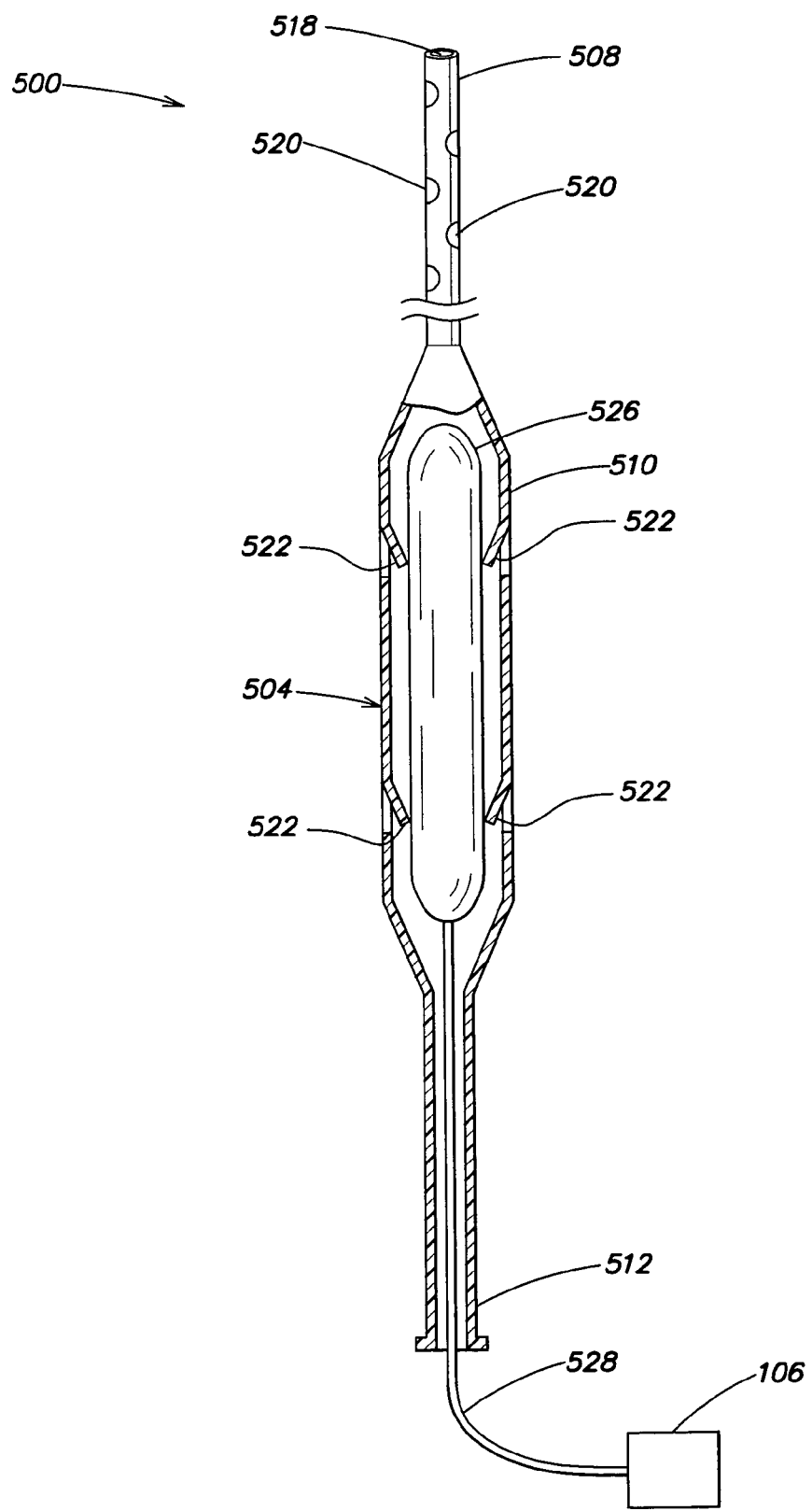
FIG. 9 is a partial cross-section view of a blood pumping system in accordance with another embodiment.

Embodiments of the present invention are described for use primarily as a left ventricle assist device with the expandable portion of a cannula located in the aorta and a distal inlet section extending into the left ventricle. Embodiments of the invention are not limited for use as left ventricle assist devices, but rather may also be used to pump blood from the right atrium or right ventricle to the pulmonary artery. A pump system 500 for use with the right atrium or right ventricle, will now be described with reference to FIG. 9. The pump system 500 includes a cannula 504 having a distal section 508, an expandable section 510 and a proximal section 512. The distal section 508 has an end outlet 518 and side outlets 520. The expandable section includes a balloon 526 coupled to a control device 106 through a lumen 528. The expandable section also includes at least one or more valves 522 that operate in a reverse manner to valves 122 discussed above, in that they open upon deflation of the balloon and close when the balloon is inflated. A one-way valve that allows blood flow from the expandable section to the end outlet, but prevents reverse flow may be included at the junction of the expandable section and the distal section.

In operation of the balloon pump system 500, the expandable section 510 is positioned in the right atrium or the right ventricle and the distal section 508 is positioned in the pulmonary artery. In such an implementation, as readily understood by those skilled in the art based on this disclosure, operation of the one-way valves in the expandable section is reversed to allow filling of the expandable section through the one-way valves during the vacuum portion of the pumping cycle and pumping of blood out of the distal section during the expansion portion of the pumping cycle. The blood pump system 500 may be percutaneously introduced into the right atrium or right ventricle.

In at least one embodiment described above, the distal section is described as a thin tube with sufficient flexibility to extend through the aorta and into the left ventricle or through the right ventricle and into the pulmonary artery. As described above, the use of a thin tube can limit the blood flow rate of blood pumps. In another embodiment, a portion, or all, of the distal section may be expandable after positioning in the left ventricle or pulmonary artery to increase blood flow. The expansion may be accomplished using, for example, one of the expansion techniques described above for the expandable section of cannulas.

In at least one embodiment, a cannula is described as having a distal section, an expandable section and a proximal section. In different embodiments, the cannula may be implemented using a single cannula or three cannulae coupled together.

In at least one embodiment described above, an inflow valve is not used with a blood pump. While there are advantages in embodiments that do not have inflow valves, in other embodiments, one or more inflow valves may be used.

While aspects of embodiments of the invention have been described for use with balloon pumps. Various aspects of embodiments of the invention may be used with pumps other than balloon pumps.

At least some embodiments of the present invention are described as including a blood pump within a cannula. The term cannula in this description is not limited to any particular type of device or tube, and includes, for example, a number of different types of implantable tubes or lumens.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A pump system for pumping blood through a body passageway, the pump system comprising:
   a distal section having at least one inlet to receive blood;
   a pumping section in fluid communication with the distal section to receive blood from the distal section, the pumping section sized to fit within a body passageway and having at least one outlet valve; and
   a balloon pump constructed and arranged to be positioned within the pumping section to draw blood into the pumping section in a first phase of operation and to pump blood out of the at least one outlet valve in a second phase of operation;
   wherein the pump system is configured such that the at least one inlet is in fluid communication with the pumping section in both the first phase of operation and the second phase of operation.

2. The pump system of claim 1, wherein the pumping section and the distal section are configured such that in the second phase of operation, a blood flow rate out of the at least one outlet valve is greater than a blood flow rate out of the at least one inlet.

3. The pump system of claim 2, wherein the pump includes a balloon that is deflated in the first phase of operation and inflated in the second phase of operation.

4. The pump system of claim 3, wherein the balloon is coupled to a lumen to supply a medium to the balloon to inflate the balloon and to extract the medium to deflate the balloon.

5. The pump system of claim 4, wherein the pump system is constructed and arranged to allow percutaneous insertion of at least the distal section and the pumping section into an artery of a patient.

6. The pump system of claim 5, wherein the pumping section includes an expandable cannula.

7. The pump system of claim 6, wherein the expandable cannula includes a channel that is configured to receive a filling medium to expand the expandable cannula.

8. The pump system of claim 2, further comprising at least one anchoring device coupled to at least one of the distal section and the pumping section, wherein the anchoring device is configurable to support the pumping section in an artery of a patient.

9. The pump system of claim 8, wherein the at least one anchoring device includes a balloon that is expandable to support the pumping section in the artery.

10. The pump system of claim 6, further comprising an extraction device constructed and arranged to receive the expandable cannula for extraction of the expandable cannula from a patient.

11. The pump system of claim 10, wherein the extraction device is constructed and arranged to collapse the expandable cannula as the expandable cannula is drawn into the extraction device for removal from the artery.

12. The pump system of claim 1, wherein the pump system is constructed and arranged to operate in a cyclical manner alternating between the first phase of operation and the second phase of operation with the first phase being longer than the second phase.

13. The pump system of claim 1, wherein the distal section is expandable from an insertion state to an operational state.

14. A method of pumping blood in a patient, the method comprising:
inserting a cannula into an artery of a patient, the cannula having a distal end with an opening and a pumping portion containing a balloon, the pumping portion being positioned within the artery and in fluid communication with the opening in the distal end and the pumping portion having at least one outlet;
drawing blood through the opening and into the pumping portion in a first phase of operation; and
pumping blood out of the at least one outlet and out of the opening in a second phase of operation.

15. The method of claim 14, wherein pumping blood includes pumping blood out of the at least one outlet at a first flow rate and pumping blood out of the opening at a second flow rate, wherein the first flow rate is greater than the second flow rate.

16. The method of claim 14, wherein blood is pumped in a cyclical manner alternating between the first phase of operation and the second phase of operation with a period of operation in the first phase being greater than a period of operation in the second phase.

17. The method of claim 14, wherein inserting the cannula includes positioning the distal end in the left ventricle of the patient's heart.

18. The method of claim 17, wherein inserting the cannula includes inserting the cannula into the femoral artery of the patient.

19. The method of claim 18, wherein the pumping portion includes an expandable section, and wherein the method further includes expanding the expandable section from an insertion state to an operational state after inserting the cannula into the femoral artery.

20. The method of claim 19, wherein pumping blood includes inflating the balloon.

21. The method of claim 20, wherein inserting the cannula includes positioning the pumping portion in the ascending aorta of the patient.

22. The method of claim 21, wherein the cannula includes at least one anchoring device, and wherein the method further includes using the at least one anchoring device to support the pumping portion in the ascending aorta.

23. The method of claim 19, further comprising moving the expandable section from the operational state to the insertion state by sliding the expandable section into an extraction device.

24. A pump system for pumping blood through a body passageway, the pump system comprising:
a distal section having at least one inlet to receive blood;
a pumping section in fluid communication with the distal section to receive blood from the distal section, the pumping section sized to fit within a body passageway, containing a balloon, and having at least one outlet valve;
means for drawing blood into the pumping section in a first phase of operation and for pumping blood out of the at least one outlet valve in a second phase of operation, such that the at least one inlet is in fluid communication with the pumping section in both the first phase of operation and the second phase of operation.

25. The pump system of claim 24, wherein the means for drawing blood includes means for drawing blood such that in the second phase of operation, a blood flow rate out of the at least one outlet valve is greater than a blood flow rate out of the at least one inlet.

26. The pump system of claim 25, wherein the pump system is constructed and arranged to allow percutaneous insertion of at least the distal section and the pumping section into an artery of a patient.

27. The pump system of claim 26, further comprising means for expanding an expandable portion of the pumping section after insertion of the pumping section into an artery.

28. The pump system of claim 27, further comprising means for anchoring the pumping section in an artery of a patient.

29. The pump system of claim 27, further comprising means for collapsing the expandable portion of the pumping section and withdrawing the pumping section from the artery.

30. The pump system of claim 24, wherein the distal section is expandable from an insertion state to an operational state.

31. A pump system for pumping blood through a body passageway, the pump system comprising:
a distal section having at least one inlet to receive blood;
a pumping section in fluid communication with the distal section to receive blood from the distal section, the pumping section sized to fit within a body passageway and having at least one outlet valve; and
a balloon pump positioned within the pumping section to draw blood into the pumping section in a first phase of operation and to pump blood out of the at least one outlet valve in a second phase of operation;
wherein the balloon pump is constructed and arranged in the pumping section to block a fluid communication path between the pumping section and the distal section in the second phase of operation to prevent blood from exiting the at least one inlet in the second phase of operation.

32. The pump system of claim 31, wherein the balloon pump includes a balloon coupled to a lumen to supply a medium to the balloon to inflate the balloon in the second phase of operation and to extract the medium from the balloon in the first phase of operation.

33. The pump system of claim 32, wherein the pump system is constructed and arranged to allow percutaneous insertion of at least the distal section and the pumping section into an artery of a patient.

34. The pump system of claim 33, wherein the pumping section includes an expandable cannula.

35. The pump system of claim 34, wherein the expandable cannula includes a channel that is configured to receive a filling medium to expand the expandable cannula.

36. A method of pumping blood in a patient, the method comprising:

inserting a cannula into the artery of a patient, the cannula having a distal end with an opening, a pumping portion, a fluid communication path between the opening and the pumping portion, and a balloon disposed in the pumping portion;

deflating the balloon to draw blood through the opening and into the pumping portion in a first phase of operation; and inflating the balloon to pump blood out of the pumping portion in a second phase of operation;

wherein inflating the balloon includes blocking the fluid communication path with a portion of the balloon.

37. The method of claim 36, wherein the pumping portion includes at least one outflow valve, and wherein inflating the balloon includes pumping blood out of the at least one outflow valve.

38. The method of claim 37, wherein inserting the cannula includes positioning the distal end in the left ventricle of the patient's heart.

39. The method of claim 38, wherein inserting the cannula includes inserting the cannula into the femoral artery of the patient.

40. The method of claim 39, wherein the pumping portion includes an expandable section, and wherein the method further includes expanding the expandable section from an insertion state to an operational state after inserting the cannula into the artery.

41. The method of claim 40, wherein inserting the cannula includes positioning the pumping portion in the ascending aorta of the patient.

42. The method of claim 36, wherein the cannula includes at least one anchoring device, and wherein the method further includes using the at least one anchoring device to support the pumping portion in the ascending aorta.

43. The method of claim 40, further comprising moving the expandable section from the operational state to the insertion state by sliding the expandable section into an extraction device.

44. A pump system for pumping blood from a patient's right atrium or right ventricle to a patient's pulmonary artery, the pump system comprising:

a distal section having at least one outlet;

a pumping section in fluid communication with the distal section to provide blood to the outlet of the distal section, the pumping section sized to fit within the patient's aorta and having at least one inlet valve to receive blood; and a pump constructed and arranged to be positioned within the pumping section to draw blood into the pumping section in a first phase of operation and to pump blood out of the outlet of the distal section in a second phase of operation.

45. The pump system of claim 44, wherein the pump includes a balloon that is deflated in the first phase of operation and inflated in the second phase of operation.

46. The pump system of claim 45, wherein the balloon is coupled to a lumen to supply a medium to the balloon to inflate the balloon and to extract the medium to deflate the balloon.

47. The pump system of claim 46, wherein the pump system is constructed and arranged to allow percutaneous insertion of at least the distal section and the pumping section.

48. The pump system of claim 47, wherein the pumping section includes an expandable cannula.

49. The pump system of claim 48, wherein the expandable cannula includes a channel that is configured to receive a filling medium to expand the expandable cannula.

50. The pump system of claim 44, wherein the at least one inlet valve is a one-way valve configured to permit flow of blood into the pumping section and prevent flow of blood out of the pumping section.

51. A method of pumping blood from a patient's right atrium or right ventricle to a patient's pulmonary artery, the method comprising:

inserting a cannula into the patient, the cannula having a distal end with at least one outlet and a pumping portion, the pumping portion containing a balloon, being positioned within the patient's aorta and in fluid communication with the opening in the distal end and the pumping portion, and having at least one inlet;

drawing blood from the right atrium or the right ventricle through the at least one inlet and into the pumping portion in a first phase of operation; and pumping blood out of the at least one outlet into the pulmonary artery in a second phase of operation.

52. The method of claim 51, wherein inserting the cannula includes positioning the distal end in the pulmonary artery and positioning the pumping portion in one of the right atrium and the right ventricle.

53. The method of claim 52, wherein the pumping portion includes an expandable section, and wherein the method further includes expanding the expandable section from an insertion state to an operational state after inserting the cannula into the patient.

54. The method of claim 53, wherein pumping blood includes inflating the balloon.

* * * * *